US006661224B1

(12) United States Patent
Linder

(10) Patent No.: US 6,661,224 B1
(45) Date of Patent: Dec. 9, 2003

(54) METHOD FOR INDUCTIVE MEASUREMENT OF A DIMENSION OF AN OBJECT

(75) Inventor: Sten Linder, Vasteras (SE)

(73) Assignee: ABB AB, Vasteras (SE)

( * ) Notice: Subject to any disclaimer, the term of this patent is extended or adjusted under 35 U.S.C. 154(b) by 0 days.

(21) Appl. No.: 10/019,441

(22) PCT Filed: Jun. 22, 2000

(86) PCT No.: PCT/SE00/01328

§ 371 (c)(1),
(2), (4) Date: Apr. 23, 2002

(87) PCT Pub. No.: WO01/01065

PCT Pub. Date: Jan. 4, 2001

(30) Foreign Application Priority Data

Jun. 30, 1999 (SE) .............................................. 9902477

(51) Int. Cl.[7] .......................... G01N 27/72; G01R 33/12
(52) U.S. Cl. ........................ 324/227; 324/229; 324/232; 324/243
(58) Field of Search ................................ 324/229, 227, 324/228, 232, 236, 239, 243

(56) References Cited

U.S. PATENT DOCUMENTS 5,059,902 A  10/1991  Linder
5,498,958 A  3/1996  Tu et al.
5,541,510 A  7/1996  Danielsson
5,552,705 A  9/1996  Keller

FOREIGN PATENT DOCUMENTS

WO  9404996  3/1994

*Primary Examiner*—Walter E. Snow
(74) *Attorney, Agent, or Firm*—Oblon, Spivak, McClelland, Maier & Neustadt, P.C.

(57) ABSTRACT

A method for non-contact measurement of dimensions such as thickness or diameter and electrical characteristics of an electrically conductive object (6) based on electromagnetic induction and a time-varying magnetic field. A substantially constant current is supplied to at least one transmitter coil (3) such that an electromagnetic field penetrates the object (6). Current to the transmitter coil (3) is cut off and a voltage induced in at least one receiving coil (8) by at least one decaying magnetic field. The voltage in receiving coil (8) is measured from a first time following decay of a magnetic field in the air (T3) until a time when the field has decayed to zero (T4, T5, T6) and the signal is integrated. A value for a physical dimension of the object (6) is calculated from this integral. The method is accurate, undisturbed by surface contamination or object movement, and applicable to different geometric forms including plate, bar or tube.

18 Claims, 3 Drawing Sheets

METHOD FOR INDUCTIVE MEASUREMENT OF A DIMENSION OF AN OBJECT

TECHNICAL FIELD

The present invention concerns the technical field of the non-contact measurement of a value for first and foremost dimensions such as thickness and diameter of an electrically conducting, substantially non-magnetic object, based on electromagnetic induction. The present invention may also be used in order to measure dimensions as stated above and at the same time as electrical characteristics of the electrically conducting object such as electrical resistivity.

The present invention may be used during the manufacture of metal products such as plate, or strip, bar or tube where it is desirable to, measure dimensions of those products. It may further be used with measurement of dimensions in connection with pyro-metallurgical processes for production of metals. The present invention may also be used for measurement of dimensions of electrically conductive objects, including non-metallic objects, in another context such as with control of characteristics of metal parts and identification of objects that cannot be seen, such as metal objects in wood in connection with sawing and so on. The present invention may further be applied in applications according to the above where, at the same time, dimensions and electrical characteristics are desired.

BACKGROUND ART

A known method for non-contact measurement of the thickness of a plate to irradiate it with a radioactive radiation or with x-rays and then measure the absorption of radiation in the plate. This absorption is dependent, amongst others, on thickness of the plate and constitutes a primary measured value for the thickness. Variations in the materials composition and coatings on the surface of the material influence the absorption of radiation and reduces thereby the accuracy of such equipment. Further, the radiation used in such equipment necessitates health and safety measures.

It is known to measure the thickness of a strip or plate of an electrically conducting object with electrical induction methods. One or more transmitting coils produce a time-varying magnetic field which can penetrate into the electrically conducting object and there induce a current. These currents in their turn produce a magnetic field which in its turn induces a voltage in one or more receiving coils and there the induced voltage is used, after some signal processing, as a measure of thickness.

Such methods and devices are often based on sinusoidally varying magnetic fields where changes in amplitude and changes in phase caused by the object are measured. Both of these changes are influenced by at least three parameters in a measuring system, object position, electrical resistance of the object and thickness of the object, and therefore such systems, in their simplest forms, become fundamentally uncertain. Attempts have been made to solve that problem by introducing measurements at different frequencies in order, in a sense, to obtain even more measured parameters, but this has given the result that interpretation of the signal becomes greatly complicated and the sufficient measurement accuracy cannot be achieved.

The above problem has been solved by using a time-varying field which is characterised by a constant current supplied to a transmitting coil over a certain time period which is then suddenly cut off, as described in U.S. Pat. No. 5,059,902. By the use of this technique an induced signal in a receiving coil is measured during at least three time intervals, one directly after current cut-off, one directly after that and before changes in the magnetic field have had time to penetrate the object of measurement, and lastly during a time interval long after current cut-off when changes in the magnetic field have had time to penetrate the object of measurement. With help of at least these three measured values the thickness of the object can be calculated.

The above method has been shown to work well in many cases, but each of the three measured values include though a degree of uncertainty. Especially where it concerns the third measured value because speed of the object influences the measured value. Altogether it means that the accuracy of the measured value for thickness is not always as desired.

A method to measure thickness of a plate is shown in U.S. Pat. No. 5,059,902, with reference to FIG. 14, by means of two coils placed on opposites sides of the plate. The plate thickness is measured in that way by measuring the distance between a coil and surface of the plate for each side respectively during a time interval directly following the cut-off of current supplied to the coils. The difference between those distances coil to plate surface and the distance between the two coils is thus the thickness of the plate. Under ordinary demands for accuracy this meter works well, but with high demands for accuracy the natural variations in distance between the coils, for example due to temperature, is a considerable problem that reduces the usability of the meter.

One way to measure the dimensions of rod and similar products during manufacture has been described in U.S. applications Ser. Nos. 09/051333 and 09/051418. The methods have been shown to be useable for measurement in many production processes such as, for example hot rolling, and even here the methods have shown limitations where the demands for measurement accuracy and stability are very high. These limitations are in a context where measurement accuracy for those types of devices is determined by the accuracy of positioning of coils in the device and the resulting sensitivity for movement in the device.

SUMMARY OF THE INVENTION

The object of the present invention is to provide a method and a device for highly accurate inductive measurement of physical dimensions such as diameter or thickness of an electrically conducting object without influence of other varying parameters such as object position and the material parameters of the object. In order to produce highly accurate measurement in practice according to the above it is a precondition that the measured value is directly simply dependent on the dimensions of the object. Further, the measurement is carried out without influence from other material in the proximity of the object, such as water, oil and surface coatings. The geometric dimension is referred to in a particular predetermined direction. Thus, for example the thickness of a flat plate is referred to as a geometric dimension perpendicular to the plane of the plate, and a bars diameter as the geometric dimension perpendicular to the long axis of the bar.

This is achieved according to the present invention by the help. of appropriately shaped coils, transmitter coils, supplied with a substantially constant current producing a magnetic field in the object. An important feature of the present invention is that the field is directed so that it has a mean component, the sum of the field, which is generally perpendicular to the desired measurement direction. After a time sufficiently long enough that the field has stabilised, the current supply to the coil is cut off.

In a similar way as described in U.S. Pat. No. 5,059,902 the measurement is begun a time after that at which current supply has been cut off. However, in U.S. Pat. No. 5,059,902, measurement is started directly at the time that current supply is cut off. In the present invention, that starting time after which measurement is begun is determined from the time that it takes for the field outside the object to decay. After the field outside the object has decayed, the measurement sequence is begun and the integration of the signal carried out under a time it takes for the field in the measurement area, the field due to the field in the object material, to decay. A measurement signal which is an integral based a voltage due to the decay of the field in the object material is the basis for determining a dimension of the object. As further described below, that time period after the decay of the field outside the object may subsequently be divided into two time intervals from which measurement signals are received which together form the basis for determining a dimension of an object independent of other parameters.

In the case that thickness of a plate is the geometric dimension desired, a desirable shape of magnetic field may be brought about according to the invention by means of positioning similar coils, transmitter coils, one on either side of the plate at the same distance from the plate and positioned opposite each other in regard to the magnetic field. When these coils are supplied with a substantially constant current no magnetic field component is produced in the direction perpendicular to the plane of the plate, the measurement direction, over the plate. In the case that the diameter of a bar or tube is the geometrical dimension that is desired, a desirable shape of the magnetic field is produced according, to the present invention by means of surrounding the bar/tube with a coil so that the bar/tube is placed in the centre of the coil.

The minimum time for which current supply should continue before it is cut off depends on the size of object and on the materials electrical resistivity. The minimum time is proportional to the square of the dimension and inversely proportional to the material electrical resistivity and is for example for an aluminium plate with thickness 2 mm of the order of 50 $\mu$-seconds. The time that should pass from current cut-off till that time which the integrated measurement should begin should be as short as possible, but, at the same time include all of the time lapse for the decay of the field outside the object. That time is determined substantially by the coils, the transmitter coils, discharge time which is determined by the inductance of the coils and the electrical components that surround the coils. Normally that time should be kept shorter than 1 $\mu$-second. The time that the integrated measurement should continue for is till substantially all field changes in the measuring area have finished, that is to say, till all significant magnetic fields have disappeared. That time is of the same order of magnitude as the minimum time current supply should continue according to the above.

Normally the changes in field are measured by means of the voltage that is induced in one or more coils, appropriately positioned. The voltage induced in such a coil is known to be proportional to dB/dt, the change in magnetic field per unit time and when the integral for this voltage is taken from the beginning time $T_{Start}$ to the end time $T_{Stop}$ this gives $$IntegralValue = K * \int_{Start}^{Stop} \frac{dB}{dt} dt = K * (B_{Tstop} - B_{Tstat}) = K * (0 - B_{Tstart})$$

where K is the proportionality constant and $B_{Stop}$=0 where the field is zero at $T_{Stop}$ means the value of the integral will be proportional to the field which, before the current cutoff, existed in the object and as well is a direct measure of the dimension of the object. If the field is substantially constant in the area where the object is, then the value of the integral will be proportional to the dimension of the object. The method according to the present invention also fulfils the goal to give an accurate measurement which is given directly from a measurement value and which is independent of everything apart from dimension.

Measuring coils for measurement of changes in magnetic field are normally placed close to the transmitting coils and symmetrically in relation to them, that being apart from that such placement is necessary for use of the method according to the invention. Measuring coils and transmitting coils may even be the same coils, but used for different functions under different time periods of the measurement. Further, the measurement may be directly measured with suitable techniques and in accordance with the above formula give the intended result for the method.

In the method according to the invention the object may move relative to the preferred position without it causing large measuring errors. With bigger movements or when the most accurate measurements are desired, another embodiment of the invention may be preferred. According to the other embodiment values may be measured, which as well as the summed changes according to the above in the two receiving coils according to the invention, may also be a difference between values from the two receiving coils, and that difference is a measurement of the position of the object.

With the use of the method for measurement of material with high electrical resistance another preferred embodiment may be used. According to that, another measurement, as well as those according to the above, the integrated induced voltage from measuring coils from time $T_{Start}$ to time $T_{Start}$, an additional integrated voltage from time $T_{Start}$ to time $T_{Start}$ is added after a fraction of the integrated voltage from $T_{Start}$ to $T1_{Start}$. That fraction has the purpose of compensating for the decay of the field outside the object which decay is not ideally fast and that during the time of that decay a certain outward diffusion of the field in the material takes place, which diffusion is not measured. The fraction may be an afterwards empirically determined and constant fraction or a more complicated, mathematically determined fraction dependent on both of the measurement values named above.

The present invention may advantageously be used in those cases when as well as an accurate measurement of a dimension as a measurement of electrical characteristics, such as electrical resistance and/or magnetic permeability is desired. The measurement is carried out according to the above with integration of two induced voltages, the first from time $T_{Start}$ to time $T_{Start}$, the second from time $T_{Start}$ to time $T1_{Start}$. In the case where electrical resistance is relatively low it is not necessary for compensation of the measurement of the dimension and the measurement value for the integrated introduced signal from $T_{Start}$ to $T1_{Start}$ may be used for calculation of the electrical resistance, which is proportional to the square of the integral value.

A SHORT DESCRIPTION OF THE DRAWINGS

The present invention will be described in more detail in connection with the enclosed drawings.

DESCRIPTION OF THE PREFERRED EMBODIMENTS

Figure 1:
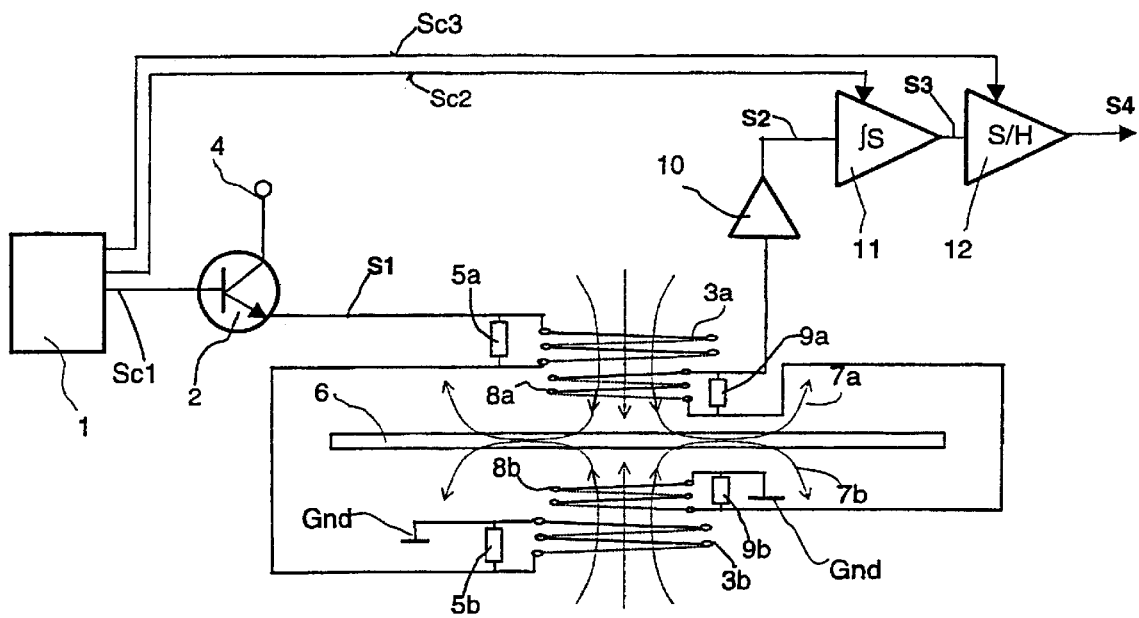
FIG. 1 shows schematically an outline diagram of a measuring device according to the invention.

In FIG. 1 an outline diagram is shown for measurement of a dimension of thickness of a plate and electrical characteristics of the material of the plate according to the present invention. This comprises a measurement object in the form of a plate 6, transmitter coils 3a and 3b, wherein a small 'a' hereafter refers to one side of the plate and b refers to the other side of the plate. Both of the transmitter coils are supplied during. a first measurement period with a substantially constant current from a current source 4 via a transistor 2 which is controlled by a control signal Sc1 from a control circuit 1. During this period of current supply the transistor conducts constant current to the connected transmitter coils 3a, 3b and further to earth at Gnd. Directly after this current supply period the current through the transmitter coils 3a, 3b is cut-off by means of stopping the current in the transistor. The resistances 5a and 5b across the transmitter coils 3a, 3b have the function of discharging the magnetic field that exists in transmitter coils 3a, 3b at current cut-off and carry that function out during a time which is, in a known way, of the order of magnitude of the coils inductance divided by the resistance.

Transmitter coils 3a and 3b are placed substantially at the same distance from the plate 6 and are similar in size. In the device illustrated the coils 3a and 3b are arranged such that the fields that are generated, 7a and 7b, are directed against each other so that the sum of the field in the centre of the plate 6, the mean component, does not have a component perpendicular to the plane of the plate 6. The whole amount of the magnetic field enclosed in the plate, the material field, is therefore dependent on the thickness of the plate 6.

Relative to the measuring area, that area that is affected by the field from transmitter coils 3a, 3b as well as the induced phenomenon brought about in the plate 6, two receiving coils 8a and 8b respectively, are arranged for detection of changes in the field in the measuring area via the voltage induced in those receiving coils 8a, 8b. These receiving coils 8a, 8b are of the same size and placed at the same distance from the plate 6 and connected together in such a way that voltage in both of the receiving coils 8a, 8b induced by a change in the field is summed. Across the receiving coils 8a, 8b discharge resistances 9a and 9b are connected which, in the same way as for the transmitter coils 3a, 3b, determine the discharge time. The voltage induced in the receiving coils 8a, 8b is amplified in an amplifier 10, from which the time varying signal S2 is formed, which is thereafter integrated in an integrator 11 during a time interval controlled by a control signal Sc2 from the control circuit 1. The signal after completed integration S3 is sent to a "Sample-and-hold" circuit 12 which takes the signal value after completed integration in the previous circuit. The signal value S4 obtained from that circuit is a stable signal value, relative to time variance, which may be used as a primary measurement value for thickness of the plate 6.

Figure 2:
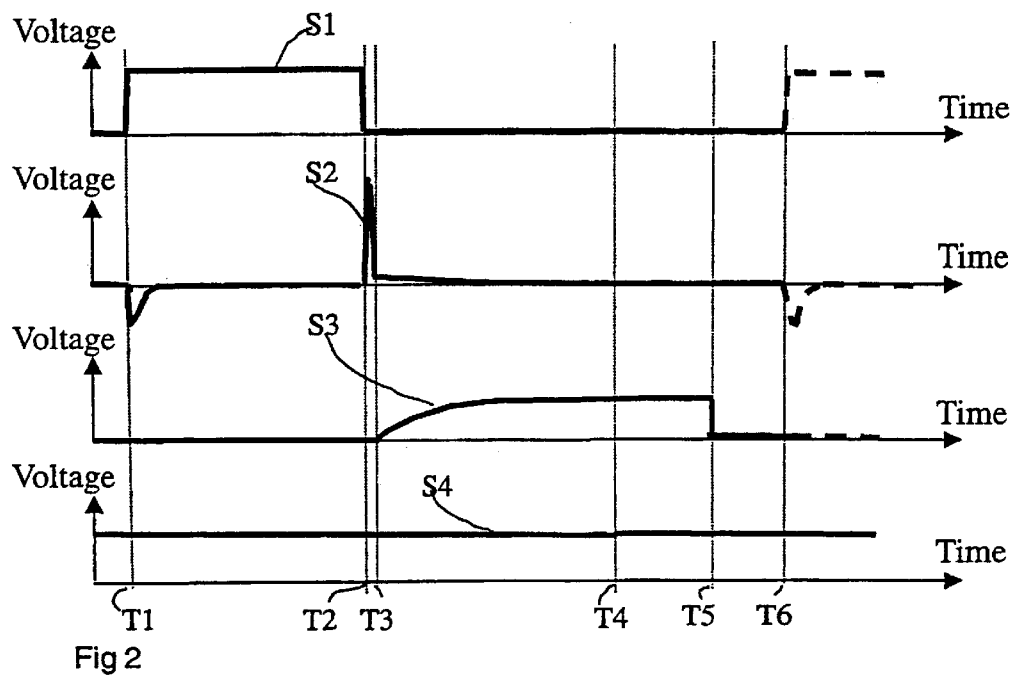
FIG. 2 shows a schematic graph of signal against time which describes time intervals during which measurement takes place according to the invention.

FIG. 2 describes the time control and signals of a device in FIG. 1 according to the illustrated invention as a graph of voltage signal against time. The topmost signal in FIG. 2 shows the voltage S1 across transmitter coils 3a and 3b against time. Control signal Sc1 to transistor 2 is high from the time T1 to the time T2 and switches therefore the transistor so that current flows through transmitter coils 3a, 3b during that time. The voltage S1 across the transmitter coils 3a, 3b becomes therefore high during that time. From time T2 to the time T6 the control signal Sc1 is low and the transistor 2 is shut off so that no current flows through the transmitter coils 3a, 3b and the voltage S1 across the transmitter coils 3a, 3b therefore becomes 0. After time T6 the sequence is repeated. During the time T1 to the time T2 the magnetic fields 7a, 7b are created and become of even strength. At time T2 the current supply to the transmitting coils 3a, 3b is suddenly cut-off, so that the magnetic fields are greatly changed. Receiving coil 8a will detect that change so that an induced voltage across that coil is proportional to the change in the magnetic field across the coil, or, $$S2 = K_c * \frac{dB}{dt}$$

where B is the time-varying magnetic field over the coil, t is time and $K_c$ is a constant of proportionality dependent on the size and shape of the coil, of the number of turns in the coil and of the amplification if the amplifier 10. K is thus only dependent on fixed variables and does not vary with variations in the object being measured, the plate 6.

As has been described in connection with U.S. Pat. No. 5,059,902 the sequence with a sudden cut-off off current supply to a coil that is in the proximity of an electrically conducting object is described by the decay of two conceptual fields, a first decay of the field outside the object and a second decay of the field in the material. There is therefore a possibility to distinguish between the decay of each of these fields, by means of the change in signal that is observed in a measuring coil, which is evident from the graph of voltage against time for signal S2, second graph from the top. Between the times T2 and T3 a decay of the field outside the object is obtained which happens quickly and gives rise to a large change in voltage in the signal during that time.

The interval begins when the current to the coil generating the field is cut-off, T2, and ends when the field in the coils, principally the transmitter coil, decays at T3. According to a known description, that decay may be determined with the expression:

$$I = I_0 * e^{-L/R*t}$$

where

I is the instantaneous current value through the coil $I_0$ is the current through the coil before cut-off L is the coils inductance R is the coils discharge resistance (5)

t is the time after current cut-off.

When I is of the order of, or less than, 1% of $I_0$ it can be said that the field has decayed. This applies if the decay time according to the above for a receiving coil is chosen approximately the same or greater than the decay time for the transmitter coil, which is to be preferred but not a necessary condition.

The time T2 to T3 which is the time under which that large change has decayed should be held as short as possible for a good measurement result and may be influenced by choice of resistances 5a, 5b, 8a and 8b according to FIG. 1. It is generally so that the higher these resistances are, the faster signal S2 decays. Normally it is worth making an effort to keep that time shorter than 1 μ-second, which with a coil of typical diameter of 50 mm and typically 10 turns means that the resistance typically should be of the order of magnitude of 100 ohm to 1000 ohm.

When the signal from the first quickly decaying part which is related to the field outside the object that has decayed away, there proceeds slow changes of the magnetic fields which are related to the decay of the material fields. As the changes here are slow the voltages that will be induced in the receiving coils 8a, 8b during the time T3 to T4 are small, which is evident from the graph for the signal S2. At the time T4 the changes have completely stopped and the signal S2 is then 0.

In the graph of voltage signal against time for the signal S3, the signal after integration in the integration circuit 11 according to FIG. 1, the third graph from the top in FIG. 2, the integrated signal is shown. The integrator 11 arranged that it is zeroed with the help of control signal Sc2 forward till the time T3 and thereafter begins integration of the signal S2. At time T4 the change in S2 has ceased, which is why S3 shows a constant value. The measurement that has been obtained from then on is a direct measurement of the extent of field that was in the plate 6 and is in that way a direct measure of the thickness of plate 6. That measure of the integral at time T4 in consequence is taken with the help of a conventional "Sample-and-hold" circuit 12 controlled by control signal Sc3. Signal S4 is therein an output signal which is directly proportional to the thickness of the plate.

The embodiment according to FIG. 1 and FIG. 2 is in no way limited but is considered to illustrate a method according to the invention. So also may transmitter and receiving coils be positioned in many ways, so long as the condition that the fields supplied by the transmitter coils meet each other in the middle of the plate so that the sum of the fields in the field direction through h the pate, in the plane of measurement, becomes zero across the plate. Normally this means that the fields meet in the centre of the plate and that the field in the field direction perpendicular to the plane of the plate becomes zero. For the receiving coils it means that they shall be substantially the same and be positioned so that they detect field changes in the plate. Receiving coils and transmitting coils may be the same coil and under particular requirements more than two receiving coils may be used.

The receiving coils may even be substituted by a direct field measuring instrument, but with the consequence that the signal is not integrated in an integrator but signal values are read off directly as they occur in time.

The control circuit 1 may be a programmed computer, a built up or programmed logic circuit or in another know way a built up control circuit. The circuit that cuts off the current supply is shown in FIG. 1 as a transistor 2 but may be any type of electrical circuit at all which has thee ability to suddenly cut-off current supply to the coil. The circuits on the receiving side are not limited except to carry out the main task of obtaining an integrated value of the voltages induced in the receiving coils between two predetermined times.

In the embodiment according to the above the current has been supplied through the transmitter coils 3a, 3b in a given direction. What that direction is has no practical significance for the present invention and that it may even be advantageous to arrange current supply so that under a period from the time T2 to the time T2 according to FIG. 2 it has a particular direction in order, subsequently, when the sequence is repeated after the time T6, to supply current in an opposite direction through the coil. The receiving channel in that case must be arranged so that it can alternately change the polarity of the signal produced in order to give a constant value, relative to time variance, for the primary signal.

Figure 3:
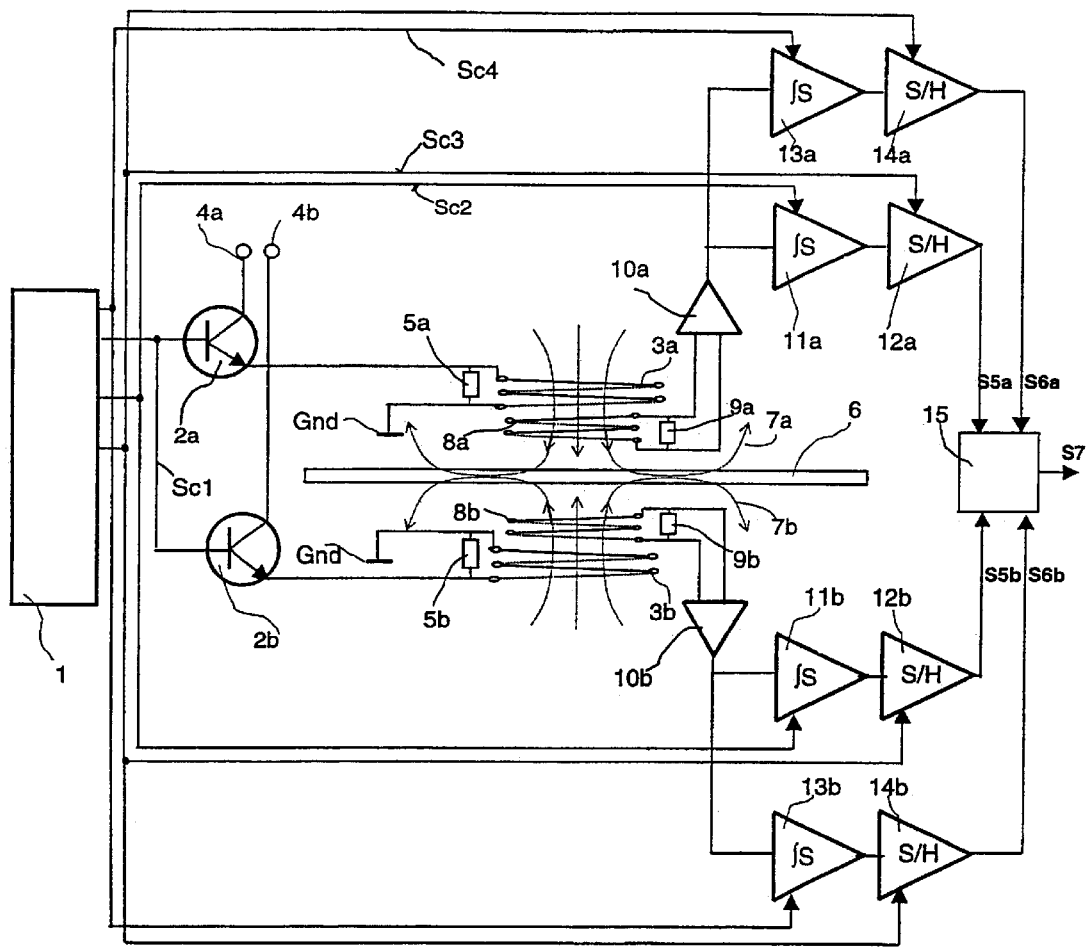
FIG. 3 shows an embodiment according to the invention for the measurement of an electrical characteristic.

Another embodiment of the present invention is shown in FIG. 3. This embodiment has the aim of solving the same measurement problem as the embodiment according to FIG. 1, but with the difference that this embodiment may be used when the position of the plate varies in the measuring area, and when the plate has a high electrical resistance. It may even be used when the plate is very thick and in that way prevents the movement of time varying signals from the one side of the plate to the other. It may even be used for the simultaneous measurement of thickness of a plate and the electrical resistivity of the material of the plate.

Figure 4:
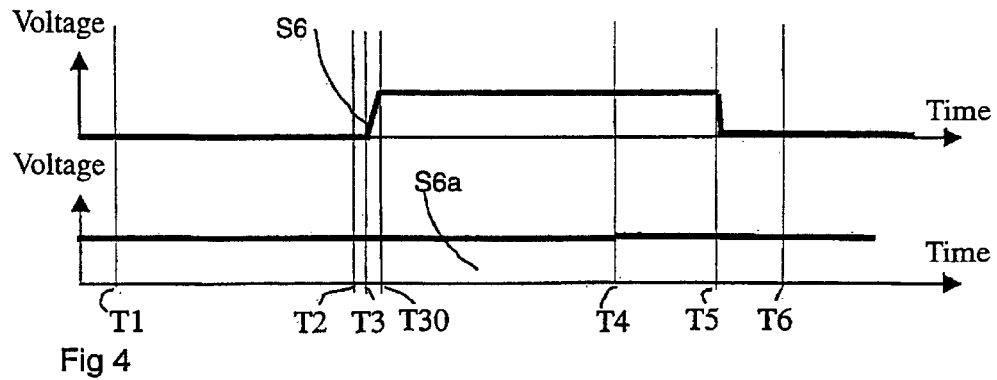
FIG. 4 shows another graph of signal against time for measurement of an electrical characteristic according to the invention.

In the embodiment according to FIG. 3 the transmitting coils 3a, 3b on each side of the platen 6 are supplied by separate but simultaneously controlled transistors, 2a and 2b respectively. The transistors 2a, 2b are thereby controlled with the same control signal, Sc1 from the control unit 1 but supplied with constant current from independent current supplies, 4a and 4b respectively. The control signal Sc1 and thereby the sequence of signals in the coils in this embodiment have the same time sequence in principle as the time sequence according to FIG. 1, but the signals are processed in separate signal channels, beginning with amplifiers 10a and 10b respectively, which in this case may be one amplifier with differential inputs. The signals from those amplifiers 10a, 10b proceed to a first part-channel 11a, 12a and 11b, 12b respectively, arranged for measurement of thickness in the same way as the channels 11 and 12 according to FIG. 1 and controlled, in principle, with the same control signals Sc2 and Sc3, while at the same time another part-channel is arranged in order to measure the integrated signal value under a first time interval during the total time T3 to the time T4, beginning with T3 and ending with the time T30, shown in the graph of voltage against time in FIG. 4. The control signal Sc4 from the control unit 1 controls those integrators, 13a and 13b respectively, in such a way that the integrators are set to zero up till the time T3 according to FIG. 2, there after the integration proceeds to go forward to the time T3., after which the integration value is held constant. At the time T5 the integrator are set to zero. The results from the above integrations are stored with the help of the "Sample-and-hold" circuits, 14a and 14b respectively.

The results from the four signal channels, S5a, S5b, S6a and S6b, are sent to a common calculation circuit 15. In that calculation circuit 15 results S5a and S5b are summed, and become in the same way according to FIG. 1 a primary measurement of the thickness of the plate 6. The difference between both of those signals, S5a–S5b, is further calculated and becomes a measure of the position of the plate 6 in the measuring area. That measurement may partly be used to measure the position of the plate and partly used in order to correct the primary measurement of thickness of the plate in respect of error depending on deviations in the plate position. In the simplest case this is done partly by subtracting the square of the difference in signal S5a–S5b, from the sum of the signals S5a+S5b according to the expression;

New primary measurement $=(S5a+S5b)-C1*(S5a-S5b)^2$ where C1 is thereby a constant which may be calculated or measured through tests with plates of different thickness. This method may also be used to correct for error due to deviations in plate position with the embodiments that have two receiving coils.

In the case that the resistivity of the plate is high or in the case that it is difficult in practice to bring about a sufficiently short decay time for the field outside the object so that the time T2 to T3 according to FIG. 2 becomes relatively long, the signals-S6a and S6b may be used in order to correct errors in the primary thickness signals by reason that decay of the material signal had begun at a time sooner than T3. The signal values of S6a and S6b respectively may be seen as an expression for the decay at time T3 and even times before that and therefore may be used in order to calculate that error. In the simplest case, the decay that takes place before T3 is proportional to the decay which took place just after T3 and which is measured between the times T3 and T30 according to FIG. 4, because;

Corrected primary signal $S5a=S5a+C2*S6a$

Corrected primary signal $S5b=S5b+C2*S6b$ where C2 is a constant which may be determined through calculation or by measurements with plates of known electrical resistance.

In the case where the plate is very thick it may sometimes be difficult to allow the time interval T3 to T4 be sufficiently long enough to allow the field from the object to decay completely, or so that the signal S2 no longer changes. A long time interval leads to long measurement times so that measurement cannot be repeated sufficiently frequently. This in turn may lead to increased disturbance or noise in the measurement. In such cases the time interval to T4 may be selected before the time that the field from the object has decayed completely and therefor measured signals may be corrected according to:

Corrected primary signal $S5a=S5a*(1-Fu(S6a/S5a))$

Corrected primary signal $S5b=S5b*(1-Fu(S6b/S5b))$

The function Fu is an unambiguous correction function with a value dependent only on the relation between the values of the integral between T3 and T30 and between T3 and T4 respectively. The function may be determined by means of carrying out measurements with plates of known thickness and known electrical resistivity. Alternatively it may be determined by mathematically solving the problem with known basic differential equations under the assumption that the field strength before current cut-off is constant across the plate and that the field is suddenly cut off.

Out of the integrated values between the times T3 and T30 the electrical resistivity may also be measured. Thereby measurements of thickness and electrical resistivity may be obtained at the same time. In the simplest case the square of the integrated measured values between T3 and T30 may be taken as a primary measurement for electrical resistivity of the material of the object.

Figure 5:
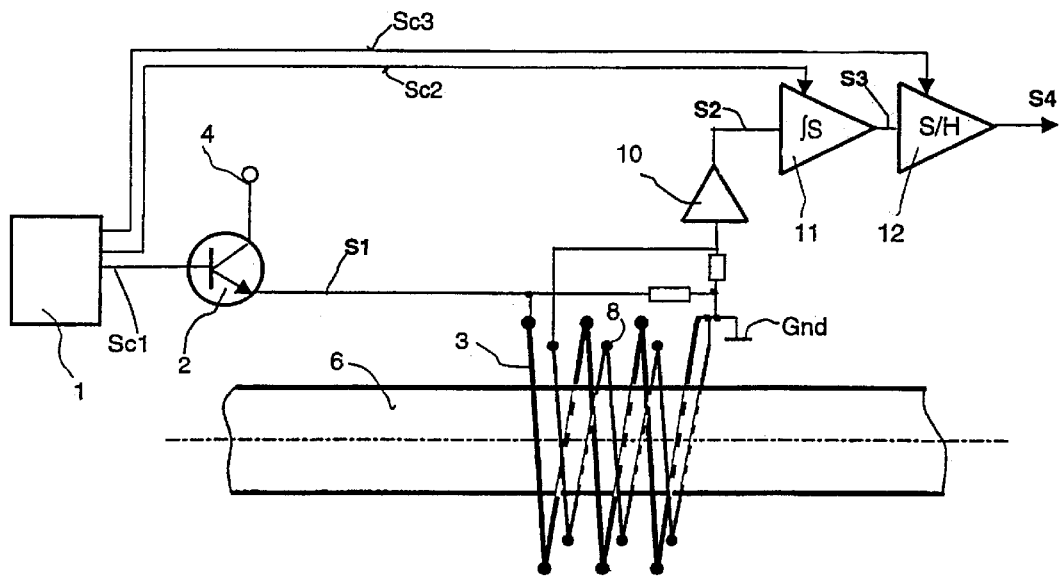
FIG. 5 shows an embodiment for measurement of a dimension of a bar according to the invention.

In FIG. 5 a device according to the present invention is shown for the measurement of dimensions of a bar, tube or wire. The object 6 is in this case a bar with cylindrical geometry where measurement of the diameter is being sought and transmitter coil 3 surrounds the object circularly symmetrically. In contrast to the device according to FIG. 1 the simpler geometry in this case makes it so that measurement may be carried out according to the invention with only one transmitter coil 3. With the form of transmitter coil illustrated the condition that the field component in the direction of measurement becomes 0 over the object is fulfilled. In the same way measurement in this case may be carried out with receiving coil 8. In general measurement is carried out in the same way according to FIG. 1. In the same way the integral of the change in field also will be a measure of the field which is stored up in the object under the period of current supply and the signal S3 and thereby the signal S4 output from "Sample-and-hold" circuit 12 will be a direct measure of the bar 6, or its diameter.

Figure 6:
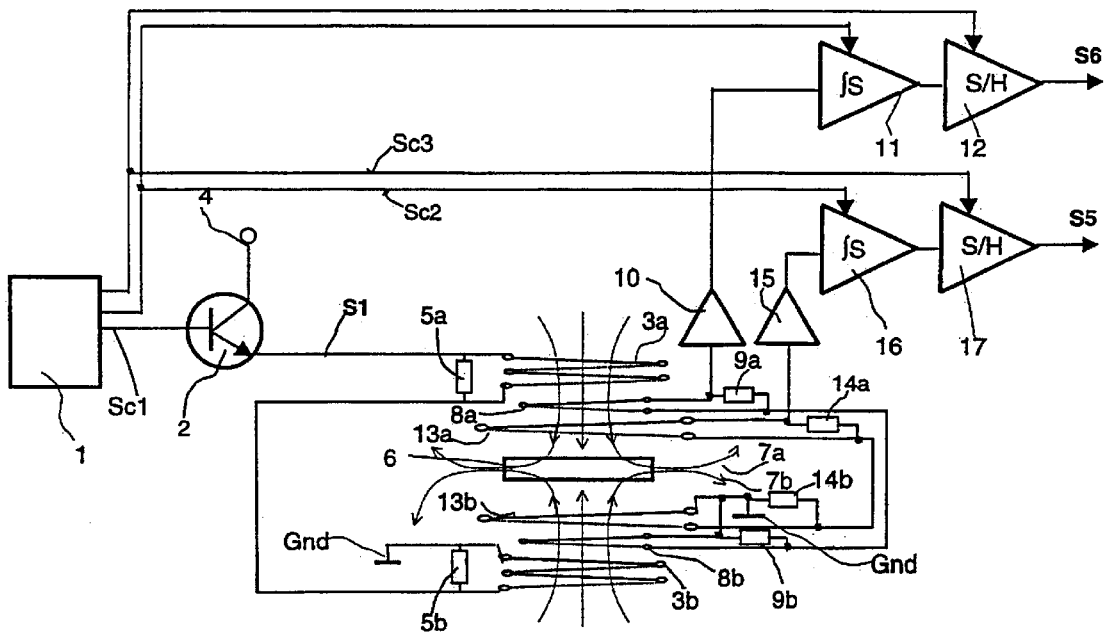
FIG. 6 shows an embodiment for measurement of two dimensions of an object at the same time according to the invention.

In FIG. 6 a device according to the present invention is shown for measurement of the dimensions of an object which has limited extension in all directions. The object 6 may be thought of as a washer, a coin or similar, for which it is desired to measure a dimension of size in more than one direction, in this case illustrated, thickness and diameter. The device consists of two transmitter coils 3a and 3b arranged relative to the object 6 and supplied with current in the same way as in the device according to FIG. 1. Symmetrically in relation to the transmitter coils 3a, 3b and to the object 6 and arranged in the same way as in FIG. 1 are two receiving coils 8a and 8b with a signal channel connected to an amplifier 10, integrator 11 and sample-and-hold circuit 12 for generating a measurement signal S5. In addition there are two further receiving coils 13a and 13b with a signal channel connected with an amplifier 15, integrator 16 and Sample-and-hold circuit 17, controlled in the same way as the above signal channel, for generating a measurement signal S6. The pairs of receiving coils 8a, 8b as well as 13a, 13b are of different size so that the smaller receiving coil pair 8a, 8b are typically of a size somewhat smaller than the object 6 and the larger receiving coil pair 13a, 13b are typically of a size somewhat larger than the object 6. Both of the measurement signals S5 and S6 are treated in a calculation unit 18, for example a microcomputer, in such a way that dimensions of thickness and diameter are obtained. This is brought about fundamentally by means of using measurement signal S5 which is dependent on both thickness and diameter, but more powerfully dependent on thickness, and measurement signal S6 which is dependent on both thickness and diameter, but more dependent on diameter. In this way, after calculation or measurements with objects of different thickness and diameters, calculation rules for calculation of thickness and diameter derived from measurement signal values of S5 and S6 may be formulated and used in the calculation unit 18.

The device according to FIG. 6 is in no way limited to the embodiment that is described in connection with the Figures, except that it may easily be realised that the measurement method for dimensions of an object according to the present invention may, where in the cases where more than one dimension is desired, be combined with a plurality of coils and a plurality of measurement channels in order to obtain a plurality of dimensions.

The invention according to the previous description has its foremost use for measuring an object that is not relatively large in size. For large objects, such as very thick plate and bar with large diameter, the time taken until changes in the magnetic field have ceased, the time T4 according to FIG. 2, is much too long to be manageable in practice. The long time in those cases means that the measurement cannot be repeated sufficiently often and, because of that, the noise level in the measurement increases which in turn leads in those cases to deteriorated measurement precision. What in those cases would be regarded as a large object also depends on electrical resistivity. For example, an aluminium plate with a thickness of the order of 10 mm may be regarded as thick. In those cases that measurement is carried out on normal as well as thick plates, or correspondingly thick bars, a meter with good functionality may be constructed by using the embodiment described for normal plate thickness, and by means of using the method described in U.S. Pat. No. 5,059,902 to measure distance between coils and surface of the plate. In an alternative embodiment of the invention this is done most simply by changing the control of the integrator Sc2 in FIG. 1 or the corresponding integrator(s) in the other Figures, to include the time interval T2 to T3 according to FIG. 2 and the other corresponding figures. In another alternative embodiment of the invention, a thick object may simultaneously have the electrical resistivity of the material of the object measured in combination with the method from U.S. Pat. No. 5,059,902. Likewise, in a further embodiment, an object that is thick in one dimension may simultaneously be measured in another dimension by selecting more than one pair of coils (8a, 8b, 13a, 13b), and sizing and placing each pair of coils relative to different dimensions of the object, such as thickness and diameter, that are to be simultaneously measured.

It is within the scope of the claims that an electrically conductive object 6 for which measurements of dimensions such as thickness as well as electrical characteristics may be measured according to the present invention, such an electrically conductive object 6 may be comprised not only of metals such as copper, aluminium and brass etc and alloys thereof, but also of non-metals, combinations and any other material capable of responding to an induced magnetic field.

What is claimed is:

1. A method for non-contact measurement of a geometric dimension of,
    and an electrical characteristic of, an electrically conductive object (6) based on electromagnetic induction and a time-varying magnetic field, in which method a substantially constant current is supplied to at least two transmitter coils (3) such that an electromagnetic field penetrates the object (6), subsequently cutting off supply of current to the transmitter coils (3), sensing a voltage induced in at least one receiving coil (8) as a result of a decaying magnetic field and integrating said sensed voltage during a time period in an interval following cutoff of current supply, characterised in that said method comprises the steps of:
        generating opposing magnetic fields by means of said at least two transmitter coils arranged one on either side of said object (6) such that said electromagnetic field penetrating said object (6) is essentially perpendicular to a measurement direction of said geometric dimension,
        measuring the voltage induced in said at least one receiving coil (8) from a first time (T3) after a decay of a magnetic field outside said object (6) as a first signal (S),
        integrating the first signal (S) from the first time (T3) following the decay of the magnetic field outside said object (6) forward till a point at which the field in the material has substantially decayed to zero (T4, T5, T6), and
        calculating from the integrated signal a value for said geometric dimension and said electrical characteristic of said object (6) from the first signal (S), and further characterised by calculating the value for said geometric dimension, said value being proportional to the integral of the first signal (S).

2. A method according to claim 1, characterised by measuring the thickness or diameter of said object (6) by integrating the first signal (S) during the time of the decay of the magnetic field that has penetrated said object (6).

3. A method according to claim 1, characterised by a further step of measuring the electrical resistivity of said object (6) by simultaneously measuring a voltage induced in said at least one coil (8) from the first time (T3) after the decay of a 10 magnetic field outside said object (6) to a second time (T30) shortly after the first time (T3) and calculating a value for electrical resistivity from that voltage as a second signal (S6).

4. A method according to claim 3, characterised by integrating the second signal (S6) during the time interval from the first time (T3) after the decay of a magnetic field outside said object (6) to the second time (T30) shortly after the first time (T3) which integral is a measure of electrical resistivity of said object (6).

5. A method according to claim 4, characterised by calculating a square of the integral of the second signal (S6) which is proportional to the electrical resistivity of said object (6).

6. A method according to claim 1, characterised by generating opposing magnetic fields such that said magnetic fields induced by each coil meet substantially in the centre of said object (6), and that the sum of the magnetic fields penetrating said object (6) is a magnetic component essentially in a direction perpendicular to the direction of measurement.

7. A method according to claim 6, characterised by
    measuring the voltage induced in said at least one receiving coil (8) from the first time (T3) after the decay of a magnetic field outside said object (6) to the second time (T30) shortly 5 after the first time (T3)
    calculating corrected primary signals $S5ak_{orr}=S5a+c2*S6a$ and $S5bk_{orr}=S5b+c2*S6b$ where $S5ak_{orr}$ and $s5b_{korr}$ are the corrected signals from the two coils 5a, S5b, S6a, S6b are results from four signal channels, and C2 is a constant and by this means correcting errors in measurement of said geometric dimension due to decay of the material field before the first time (T3).

8. A method according to claim 6, characterized by the step of
    adding a fraction of the integral of the signal during the interval from the first time (T3) after the decay of a magnetic field outside said object (6) until the second time (T30) to the original measured first signal (S).

9. A method according to claim 6, characterized by the step of
    calculating a corrected primary signal $S5ak_{o'''}=S5a-S5a*Fu(S6a/S5a)$ and $S5b_{k_{o'''}}=S5b-S5b*Fu(S6b/S5b)$ where S5a, S5b, S6a, S6b are the results from the four signal channels and Fu is a function dependent only on the relation between the values of the integral between; the first time (T3) and the second time (T30), and between the first time (T3) and a third time to the decay of the material field (T4), as a method to calculate a value for the third time (T4) when decay of the material field takes place over a long time interval.

10. A method according to claim 3, characterised by the steps of
    using more than one pair of receiving coils (8a, 8b, 13a, 13b),
    selecting the sizes of the coils in relation to different geometric dimensions of the said object (6) such that more than one geometric dimension, such as thickness and diameter, may be calculated from signals received in more than one pair of receiving coils (8a, 8b, 13a, 13b).

11. A method according to claim 1, characterised in that the said object (6) comprises a metal or metal alloy.

12. A method according to claim 1, characterised in that the said object (6) comprises a non-metal.

13. A method according to claim 1, characterised in that the said object (6) comprises a combination of different metals and/or metal alloys.

14. A method according to claim 3, characterised by the further steps of calculating a first value from the first signal (S) during a time interval between the time of cutting off current supply (T2) and the first time (T3) as a distance between a transmitter coil (3) and a surface of the object (6)

calculating from the first value and a distance between the transmitter coils (3a, 3b) said geometric dimension of the object (6).

15. A method according to claim 14, characterised by the further steps of arranging more than one pair of receiving coils (8a, 8b, 13a, 13b)

selecting the sizes of the coils in relation to different geometric dimensions of the said object (6) such that more than one geometric dimension such as thickness and diameter may be calculated from signals received in more than one pair of receiving coils (8a, 8b, 13a, 13b).

16. A method according to claim 10, characterised by the further steps of calculating a first value from the first signal (S) during a time interval between the time of cutting off current supply (T2) and the first time (T3) as a distance between a transmitter coil (3) and a surface of the object (6)

calculating from the first value and a distance between the transmitter coils (3a, 3b) said geometric dimension of the object (6).

17. A method according to claim 16, characterised by the further step of calculating a value for the square of the second signal (S6) from the first time (T3) to the second time (T30) shortly after the first time (T3) thus providing a value proportional to the electrical resistivity of said object (6).

18. A device and system for carrying out a method for non-contact measurement of a geometric dimension of, and an electrical characteristic of, an electrically conductive object (6) according to claim 1, comprising at least two transmitter coils (3a, 3b) arranged one on either side of said object (6) so as to generate opposing electromagnetic fields such that said electromagnetic field penetrating said object (6) is essentially perpendicular to a measurement direction of said geometric dimension.

* * * * *